US00PP08509P

United States Patent [19]

Moore

[11] Patent Number: Plant 8,509

[45] Date of Patent: Dec. 21, 1993

[54] ORNAMENTAL DWARF PEACH—TOM THUMB CULTIVAR

[75] Inventor: James N. Moore, Fayetteville, Ark.

[73] Assignee: University of Arkansas, Fayetteville, Ark.

[21] Appl. No.: 952,302

[22] Filed: Sep. 28, 1992

[51] Int. Cl.[5] ..... A01H 5/00

[52] U.S. Cl. ..... Plt./42.1

[58] Field of Search ..... Plt./43.3, 42.1

[56] References Cited

U.S. PATENT DOCUMENTS

P.P. 306 11/1938 Maillochon et al. ..... Plt. 42.1

OTHER PUBLICATIONS

Voss, Donald H. 1992, "Relating Colorimeter Measurement of Plant Color to the *Royal Horticultural Society Colour Chart*" *Hort Science*, vol. 27 (12) pp. 1256–1260.

Anon. 'Thom Thumb' *Plant Patent Directory* National Assn. of Plant Patent Owners 1990 p. 0088.

*Primary Examiner*—James R. Feyrer

[57] ABSTRACT

Description and specifications of a new and distinct ornamental dwarf peach variety which originated from the germination of open-pollinated seeds of the Tsukuba #2 peach rootstock variety (non-patented) are provided. This new ornamental dwarf peach variety can be distinguished by its dwarf plant size, persistent dark red foliage, and symmetrical plant shape.

2 Drawing Sheets

SUMMARY OF THE INVENTION

The new and distinct variety of ornamental dwarf peach originated from open-pollinated seeds of Tsukuba #2 (non-patented), a Japanese rootstock variety, collected in 1984 at the Arkansas Agricultural Experiment Station at Clarksville, Ark. The seeds resulting from this collection were planted in 1985 in a field of the Arkansas Agricultural Experiment Station at Clarksville, Ark. The selection was made in the field in 1988 and designated Ark. 84186-T-3. This plant was selected for its dwarf plant stature, attractive dark red leaves, and double, pink-red flowers.

During 1988, the original plant selection was propagated asexually by budding onto peach rootstocks at the above noted location. Subsequently, the new variety has been asexually propagated by budding onto peach rootstocks and by the rooting of softwood cuttings. It roots well from softwood cuttings and no incompatibility with peach rootstocks has occurred following budding. Following both types of asexual multiplication, the vegetative and flowering characteristics of the original plant have been maintained.

Plants of the new variety exhibit the typical genetic dwarf growth habit. In breeding, the dwarf tree habit is transmitted as a single recessive gene, which could serve as a source of dwarf plant habit in breeding small stature trees for intensive cultural systems. They produce a dense, much-branched shrub-type of growth which reaches only about five feet in height in five years. Leaves are no longer than those of standard peach trees, normally reaching 7 to 10 inches in length.

Leaves of the new variety are dark red in color and retain the red color throughout the growing season. Flowers are double, pink-red in color, and are produced in mid-March in central Arkansas. Fruits are round, pubescent, small, and of poor eating quality.

The distinctive features of the new variety are its much dwarfed growth habit, its attractive dark red leaf coloration and its attractive pink-red flowers. Its value is as an ornamental dwarf shrub where red leaf color is desirable in the landscape, or as a containerized patio plant.

The new variety has been named the Bonfire cultivar.

BRIEF DESCRIPTION OF THE PHOTOGRAPHS

In the accompanying drawing, a first sheet of the photographic drawing depicts a typical mature specimen of 'Bonfire' in perspective view, showing the unusual tree size and shape, very heavy canopy density due ot its very short internodes, and the unique leaves of this variety which characteristically exhibit a novel combination of unusual color when forming and newly formed, large size, and an attrctive wavy margin and deep green color when mature. A second sheet of drawing depicts the tree approching full bloom stage and indicates the characteristics of mature bark color and texture, the branching and trunk characters of this tree, and the high density of the large, double, showy pink blossoms produced by this tree which is highly ornamental in both spring and summer.

DETAILED DESCRIPTION OF THE NEW VARIETY

The following is a detailed description of the botanical and pomological characteristics of the subject ornamental dwarf peach. Color data are readings from a Minolta Chroma Meter CR-200, version 3.0 which measures absolute chromaticity in tristimulus values X, Y, and Z as determined by the Commission Internationale de l'Eclairage. Color was determined using the CIE Yxy system. Calibration was performed using a standard white plate supplied by the manufacturer. These color data are supplemented with The Royal Horticultural Society Colour Chart designations obtained by computer matching of electronic readings to R.H.S. color references.

Where dimensions, sizes, colors and other characteristics are given, it is to be understood that such characteristics are approximations of averages set forth as accurately as practicable.

The descriptions reported herein are from specimens grown at Clarksville, Ark.

Plant:

*Size.*—Dwarf, for trees 5 years of age: height=162.6 cm; width=215.9 cm.

*Form.*—Dense, much-branched shrub-type growth habit.

*Cold hardiness.*—Hardy to −23° C.

*Disease Resistance.*—Resistant to bacterial leaf spot.

Foliage:

*Shoots.*—Mature shoot length 36.8 cm; diameter base 9.6 mm, midpoint 8.4 mm, terminal 7.4 mm. Mature shoot color: base Y=10.66, x=0.3739, y=0.3563, Brown (200D); midpoint Y=9.61, x=0.3835, y=0.3603, Brown (200D); terminal Y=10.61, =0.3862, y=0.3632, Brown (200D). Young shoot color: base: Y=7.12, x=0.3928, y=0.3586, Brown (200C); midpoint Y=8.51, x=0.3773, y=0.3618, Brown (200C); terminal Y=10.33, x=0.3797, y=0.3674, Brown (200C).

*Internode length.*—7–11 mm, avg. 8 mm.

*Leaves.*—Mature leaf size: length 18.54 cm; diameter at widest point 3.36 cm. Mature leaf color: abaxial base Y=7.45, x=0.3390, y=0.3578, Greyed-Purple (187A); midpoint Y=6.76, x=0.3385, y=0.3575, Greyed-Purple (187A); terminal Y=6.52, x=0.3381, y=0.3505, Greyed-Purple (187A); adaxial base Y=6.91, x=0.3415, y=0.3525, Greyed-Purple (187A); midpoint Y=6.69, x=0.3405, y=0.3481, Greyed-Purple (187A); terminal Y=6.52, x=0.3396, y=0.3462, Greyed-Purple (187A). Petiole length: 12.2 mm. Leaf glands: reinform, 2–4 per leaf, avg. 3.2. Located on lower portion of leaf blade near juncture with petiole.

Bark:

*Color.*—New wood: Brown Group (200C); Mature wood: Brown Group (200D).

*Texture.*—Smooth.

*Lenticels.*—Density: 5 per $cm^2$; Shape: horizontal oblong; Size: horizontal, 1.5–3.0 mm, avg. 2.25 mm; vertical, 1–2 mm, avg. 1.2 mm.

Flowers:

*Date of bloom.*—First, Mar. 17; 50%, Mar. 22; Full, Apr. 1.

*Flower diameter.*—3.5 cm, large, showy, double.

*Petals per flower.*—5.

*Flowers per cluster.*—1.

*Flower color.*—Pink-red, Red-Purple Group (62D).

*Pollen.*—Present and normal.

Fruit:

*Size.*—Small.

*Pubescence.*—Heavy.

*Color.*—Dull, greenish-yellow.

*Flesh.*—Thin, dry, fibrous.

*Adherence to stone.*—Semi-clingstone.

*Quality.*—Poor.

Seed:

*Size.*—Length 31.0 mm; width 25.1 mm.

*Shape.*—Slightly oblong, with prominent suture and beak, deeply furrowed surface.

*Color.*—Greyed-Orange Group (167C).

Use: Ornamental plant where small size and red foliage color is desired in landscape, and as contained ornamental patio plant.

The Variety

The most distinctive features of the variety are its dwarf growth habit and its attractive red foliage and desirable plant form.

I claim:

1. A new and distinct variety of ornamental dwarf peach, substantially as illustrated and described, characterized by its dwarf stature, dark red peristent foliage, and attractive plant form.

* * * * *

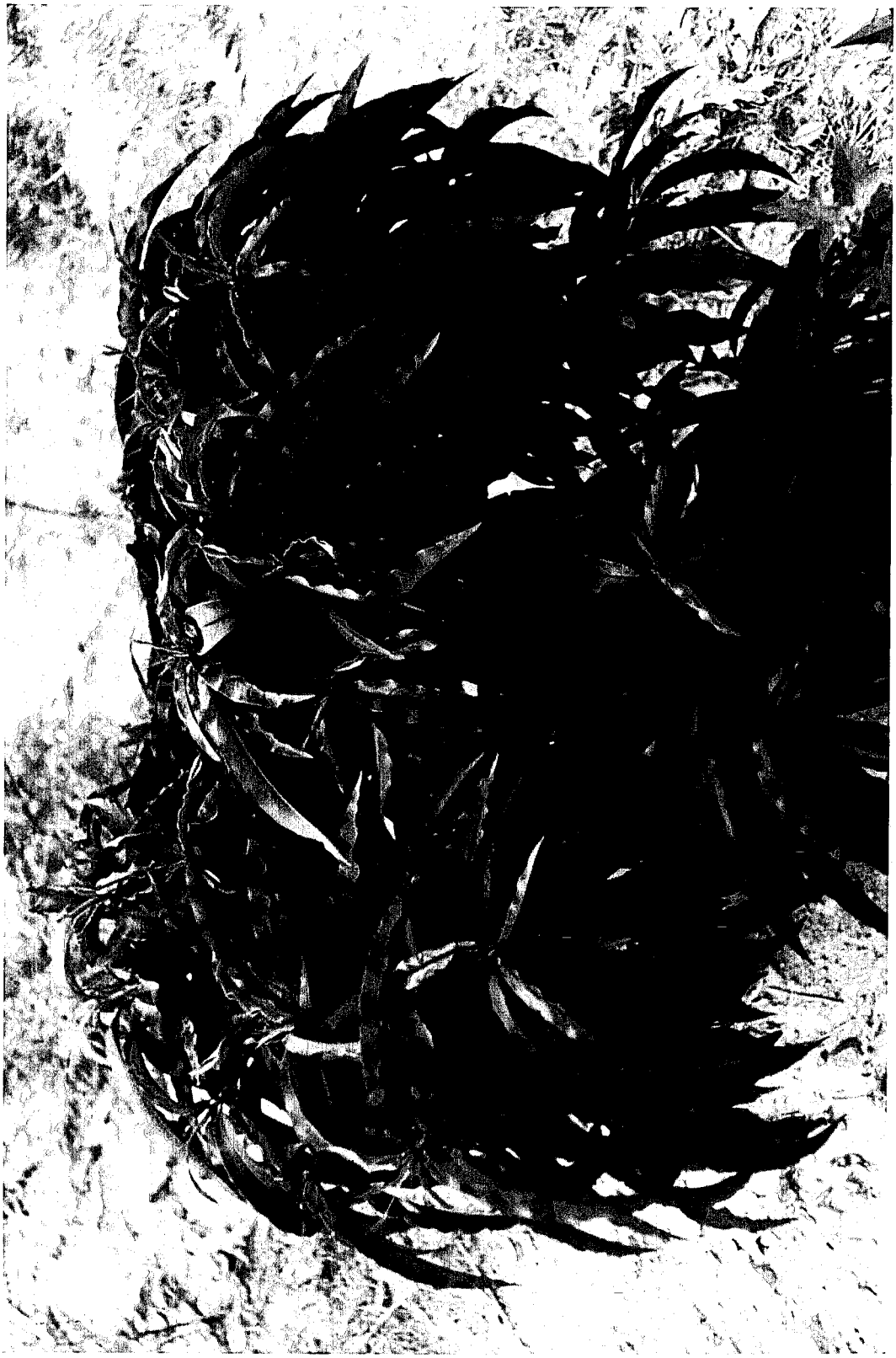

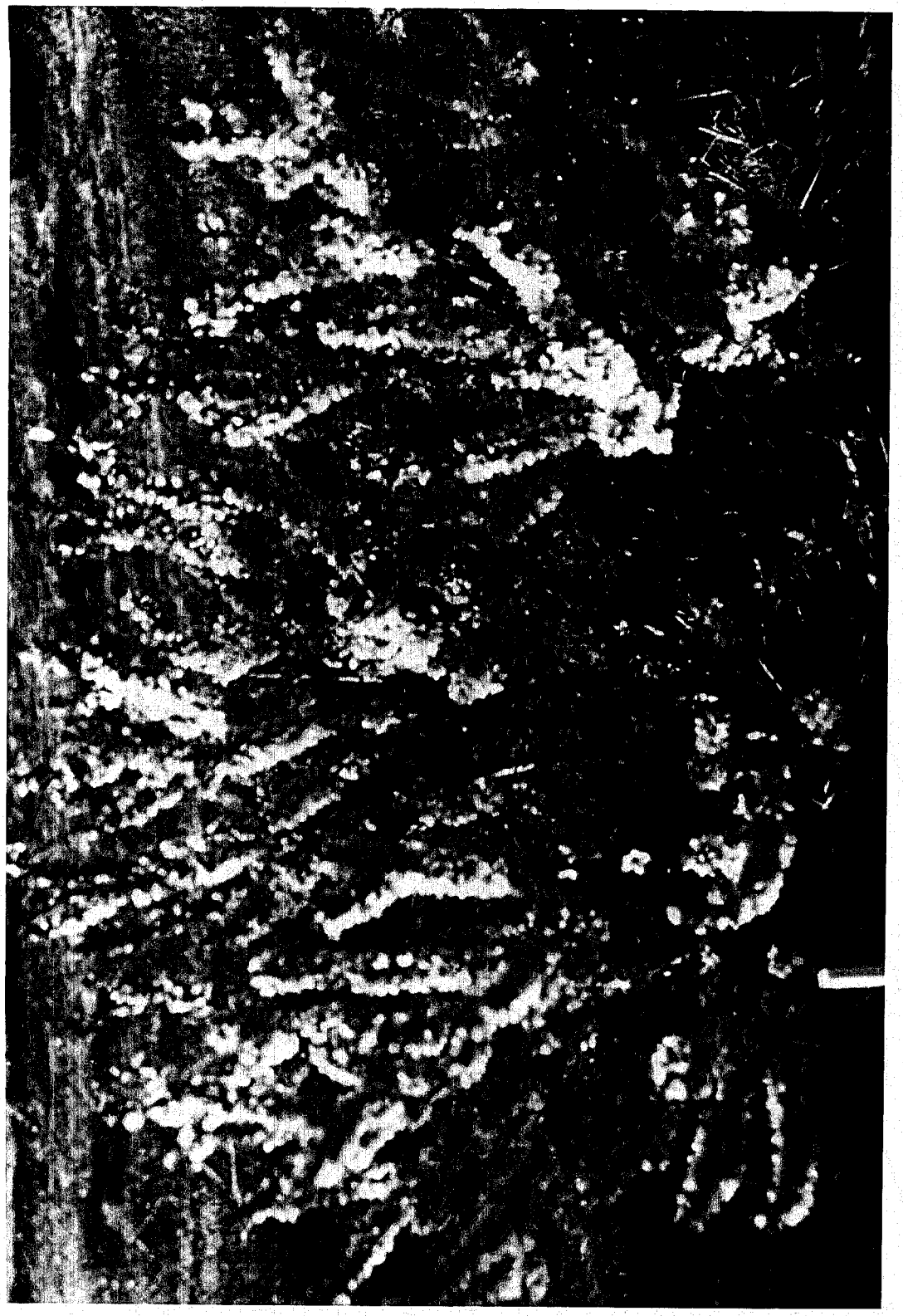

UNITED STATES PATENT AND TRADEMARK OFFICE

CERTIFICATE OF CORRECTION

PATENT NO. : Plant 8,509

DATED : December 21, 1993

INVENTOR(S) : James N. Moore

It is certified that error appears in the above-indentified patent and that said Letters Patent is hereby corrected as shown below:

On title page,

In the title, item 54, change"-Tom Thumb" to --BONFIRE--.

Signed and Sealed this

Twenty-third Day of July, 1996

Bruce Lehman

*Attest:*

BRUCE LEHMAN

*Attesting Officer*

*Commissioner of Patents and Trademarks*